(12) United States Patent
Shimogami et al.

(10) Patent No.: US 8,540,695 B2
(45) Date of Patent: Sep. 24, 2013

(54) CATHETER

(75) Inventors: Manabu Shimogami, Nagoya (JP); Nobuyoshi Watanabe, Nagoya (JP)

(73) Assignee: Asahi Intecc Co., Ltd., Nagoya-shi (JP)

( * ) Notice: Subject to any disclaimer, the term of this patent is extended or adjusted under 35 U.S.C. 154(b) by 386 days.

(21) Appl. No.: 12/575,032

(22) Filed: Oct. 7, 2009

(65) Prior Publication Data

US 2010/0094258 A1 Apr. 15, 2010

(30) Foreign Application Priority Data

Oct. 11, 2008 (JP) .................................. 2008-264696

(51) Int. Cl.
*A61M 31/00* (2006.01)

(52) U.S. Cl.
USPC ........................................................ 604/525

(58) Field of Classification Search
USPC ................................. 604/523–527
See application file for complete search history.

(56) References Cited

U.S. PATENT DOCUMENTS

| | | | |
|---|---|---|---|
| 3,815,608 A | 6/1974 | Spinosa et al. | |
| 4,654,024 A | 3/1987 | Crittenden et al. | |
| 4,883,458 A | 11/1989 | Shiber | |
| 4,886,490 A | 12/1989 | Shiber | |
| 4,898,575 A | 2/1990 | Fischell et al. | |
| 5,019,057 A | 5/1991 | Truckai | |
| 5,041,082 A | 8/1991 | Shiber | |
| 5,078,723 A | 1/1992 | Dance et al. | |
| 5,127,917 A | 7/1992 | Niederhauser et al. | |
| 5,131,406 A | 7/1992 | Kaltenbach | |
| 5,254,107 A * | 10/1993 | Soltesz ........................ | 604/525 |
| 5,314,438 A | 5/1994 | Shturman | |
| 5,554,139 A | 9/1996 | Okajima | |
| 5,702,373 A | 12/1997 | Samson | |
| 6,171,296 B1 | 1/2001 | Chow | |
| 6,296,631 B2 | 10/2001 | Chow | |
| 6,358,238 B1 | 3/2002 | Sherry | |
| 6,508,806 B1 * | 1/2003 | Hoste ........................... | 604/524 |
| 6,589,227 B2 | 7/2003 | Klint | |
| 6,824,553 B1 * | 11/2004 | Samson et al. ............... | 606/192 |
| 6,881,194 B2 | 4/2005 | Miyata et al. | |
| 2001/0044633 A1 | 11/2001 | Klint | |
| 2002/0032408 A1 | 3/2002 | Parker et al. | |

(Continued)

FOREIGN PATENT DOCUMENTS

| | | |
|---|---|---|
| EP | 0661072 A1 | 7/1995 |
| JP | 08-071157 A | 3/1996 |

(Continued)

OTHER PUBLICATIONS

EP Office Action for corresponding EP Application No. 09172579.6 mailed on Jun. 6, 2011.

(Continued)

*Primary Examiner* — Kevin C Sirmons
*Assistant Examiner* — Bradley Osinski
(74) *Attorney, Agent, or Firm* — Oliff & Berridge, PLC (57) ABSTRACT

A catheter body includes a hollow coil whose outer and inner surfaces are coated with outer and inner resin layers. A resin tip is provided at a distal end of the catheter body. The tip has a tapered section at a distal end of the tip. Also, an axially extending braid is embedded in the catheter body and the tip to extend from the catheter body to the tip.

9 Claims, 10 Drawing Sheets

(56) References Cited

U.S. PATENT DOCUMENTS

| | | | |
|---|---|---|---|
| 2003/0191451 A1* | 10/2003 | Gilmartin | 604/527 |
| 2003/0216761 A1 | 11/2003 | Shiber | |
| 2004/0010243 A1 | 1/2004 | Klint | |
| 2004/0082879 A1 | 4/2004 | Klint | |
| 2004/0249277 A1 | 12/2004 | Kato et al. | |
| 2005/0022572 A1 | 2/2005 | Kato et al. | |
| 2005/0027309 A1 | 2/2005 | Shiber | |
| 2005/0154400 A1 | 7/2005 | Kato et al. | |
| 2005/0222585 A1 | 10/2005 | Miyata et al. | |
| 2006/0089618 A1 | 4/2006 | McFerran et al. | |
| 2006/0095050 A1* | 5/2006 | Hartley et al. | 606/108 |
| 2006/0142704 A1 | 6/2006 | Lentz | |
| 2006/0178653 A1 | 8/2006 | Shimogami et al. | |
| 2007/0060996 A1 | 3/2007 | Goodin et al. | |
| 2007/0208368 A1* | 9/2007 | Katoh et al. | 606/198 |
| 2008/0287786 A1 | 11/2008 | Lentz | |

FOREIGN PATENT DOCUMENTS

| | | |
|---|---|---|
| JP | 9-149938 A | 6/1997 |
| JP | 2003-508132 A | 3/2003 |
| JP | 2005-296078 | 10/2005 |
| JP | 2006-174959 A | 7/2006 |
| JP | 2007-23373 A | 2/2007 |
| JP | 2007-236472 A | 9/2007 |
| JP | 2008-110132 A | 5/2008 |
| JP | 2008-183226 | 8/2008 |
| JP | 2008-229160 A | 10/2008 |
| WO | 03086519 A1 | 10/2003 |

OTHER PUBLICATIONS

European Patent Office Extended Search Report dated Jan. 20, 2010 for related EP Application No. 09172579.6.

JP Office Action with English Summary for JP Application No. 2008-264696 mailed on Dec. 28, 2010 (4 pages).

Aug. 24, 2012 Notification of Reasons for Refusal issued in Japanese Patent Application No. 2011-039209 (with translation).

Nov. 5, 2012 Second Office Action issued in Chinese Patent Application No. 2009102040534 (with translation).

Mar. 1, 2012 First Office Action issued in Chinese Patent Application No. 2009102040534 (with translation).

* cited by examiner

CATHETER

BACKGROUND OF THE INVENTION

1. Field of the Invention

The present invention relates to a catheter including a catheter body including a coil.

2. Description of the Related Art

Catheters have been used while being inserted into tubes and body tissues of human bodies, such as vessels, alimentary canals, ureters, etc. A catheter known as one type of such catheters includes a catheter body including a coil, the coil formed such that a plurality of metal strands are wound or stranded (see Japanese Unexamined Patent Application Publication Nos. 2005-296078 or 2006-174959). In the catheter, the coil of the catheter body may be coated with resin and include a cylindrical resin tip at the distal end (distal point) of the catheter. The tip has a tapered section. (For example, see US Patent Application Publication No. 2007/0208368.)

Since the catheter includes the catheter body including the coil, good torque transmission performance is provided. For example, the catheter has been preferably used for an operation of dilating a stenosis, in particular, a substantially completely occluded stenosis or an occlusion of a vessel, and allowing blood to flow therethrough.

The catheter, in which the catheter body includes the coil coated with resin and the tapered resin tip is provided at the distal end of the catheter, has been preferably used to pass through a vessel called a collateral channel, in controlled antegrade and retrograde tracking (CART) approach, which is a new operation in cardiac catheter treatment applied to a lesion of a severe stenosis called a chronic total occlusion (CTO).

The diameter of the collateral channel may be small. In addition, the collateral channel may have a branch at an acute branching angle of 90° or smaller with respect to a main vessel. The tapered resin tip at the distal end of the catheter can enter the branch at an acute angle without damaging an inner surface of the vessel. The catheter body including the coil provides high torque transmission performance. Thus, the catheter can be smoothly advanced through the collateral channel including the branch while the catheter dilates the collateral channel.

SUMMARY OF THE INVENTION

The inventors have studied the structure of the catheter of the related art, in which the tapered resin tip is provided at the distal end of the catheter body including the coil. The catheter of the related art still has some points to be improved for further desirably carrying out the CART approach, and for advantageously carrying out various operations other than the CART approach.

In the catheter of the related art, the resin tip is sufficiently softer than the catheter body including the coil. For example, when the tip and the catheter body pass through a branch of a vessel at an acute branching angle while the tip and the catheter body are bent at an acute angle corresponding to the branching angle, stress may be concentrated at the boundary between the proximal end of the tip and the distal end of the coil of the catheter body because the softness of the tip differs from the softness of the catheter body including the coil. Also, torsional stress may be concentrated at the boundary between the proximal end of the tip and the distal end of the catheter body when the tip reaches a stenosis and the catheter body is rotated while rotation of the tip is stuck, for example, because the stenosis catches the distal end of the tip. Moreover, since the tip is soft, the torque transmissivity between the catheter body and the tip is likely decreased.

In light of the above situations, an object of the invention is to provide a catheter in which a tapered resin tip is provided at the distal end of a catheter body including a coil, the catheter being sufficiently soft and reliably providing good torque transmission performance. Another object of the invention is to provide a structure of the catheter which is improved to advantageously decrease a stress concentrated at the boundary between the distal end of the catheter body and the proximal end of the tip, and to advantageously increase the torque transmission performance at the boundary.

The invention may be preferably carried out according to aspects described below to attain the objects, and address the drawbacks of the related art described above and objects apparent from the specification and drawings of the invention. The aspects and technical features of the invention are not limited to those described below. The aspects and technical features of the invention should be recognized and understood on the basis of the scope of the invention disclosed in the specification and drawings.

A catheter according to an aspect of the invention includes a catheter body, a tip, and a braid. The catheter body includes a hollow coil in which a plurality of metal strands are wound or stranded, an inner resin layer arranged on an inner surface of the coil and having a lumen therein, and an outer resin layer arranged on an outer surface of the coil. The tip is made of resin and provided at a distal end of the catheter body. The tip has a tapered section with a diameter decreasing toward a distal side. The tip has an inner bore communicating with the lumen of the inner resin layer. The braid extends in an axial direction of the catheter body from a proximal section of the tip to at least a distal section of the coil. The braid is positioned between the inner resin layer and the coil in the catheter body.

A catheter according to another aspect of the invention includes a catheter body, a tip, and a braid. The catheter body includes a hollow coil in which a plurality of metal strands are wound or stranded, an inner resin layer arranged on an inner surface of the coil and having a lumen therein, and an outer resin layer arranged on an outer surface of the coil. The tip is made of resin and provided at a distal end of the catheter body. The tip has a tapered section with a diameter decreasing toward a distal side. The tip has an inner bore communicating with the lumen of the inner resin layer. The braid extends in an axial direction of the catheter body from a proximal section of the tip to at least a distal section of the coil. The braid is positioned between the inner resin layer and the outer resin layer in the catheter body.

A catheter according to still another aspect of the invention includes a catheter body, a tip, an inner layer, and a braid. The catheter body includes a hollow coil in which a plurality of metal strands are wound or stranded, an inner resin layer with which an inner peripheral surface of the coil is coated, and an outer resin layer with which an outer peripheral surface of the coil is coated. The tip is formed of a resin cylindrical member and provided at a distal end of the catheter body. A distal section of the tip defines a tapered section with a diameter decreasing toward a distal side. The tip has an inner bore communicating with a hollow portion of the catheter body. The inner-layer extending portion is formed such that the inner resin layer continuously extends from the distal end of the catheter body. The inner-layer extending portion defines an inner peripheral portion of the proximal section of the tip. The braid is formed of a plurality of braided strands. The braid is positioned in an axial direction of the catheter body and extends from the proximal section of the tip to at least a distal section of the catheter body. The braid is arranged at the inner-layer extending portion in the tip and at the inner resin layer of at least the distal section of the catheter body.

With the catheter according to any of the aspects of the invention, the catheter body includes the coil, and the resin tip is provided at the distal end of the catheter body, the tip having the tapered section at the distal section of the tip. Accordingly, sufficiently high flexibility and reliable good torque transmission performance, i.e., torque transmissivity, can be provided.

With the catheter according to any of the aspects of the invention, the braid axially extends from the proximal section of the tip to at least the distal section of the catheter body. Hence, if the catheter body is rotated while the boundary between the distal end of the catheter body and the proximal end of the tip is bent at an acute angle of 90° or smaller or while the rotation of the tip is stuck, the braid can disperse the stress generated at the boundary over a wide area extending from the distal section of the catheter body to the proximal section of the tip. Thus, the stress concentrated at the boundary between the distal end of the catheter body and the proximal end of the tip can be advantageously decreased. In addition, the torque transmission performance at the boundary between the distal end of the catheter body and the proximal end of the tip can be advantageously increased while the proximal section of the tip maintains flexibility because of the braid embedded in the proximal section of the tip, as compared with the case where the tip is made of only a resin material. Also, a sudden change in softness or flexibility at the boundary between the catheter body and the tip can be advantageously decreased. This can effectively decrease the stress concentrated at the boundary.

With the catheter according to any of the aspects of the invention, the catheter operation using advanced techniques, such as the CART approach, in which the catheter is inserted through a vessel having a branch with a small diameter at an acute branching angle of 90° or smaller with respect to a main vessel, like a collateral channel, can be safely and smoothly carried out without the vessel or the catheter being damaged.

DESCRIPTION OF THE PREFERRED EMBODIMENTS

A configuration of a catheter according to an embodiment of the invention will be described in detail below with reference to the attached drawings, to specifically clarify the invention.

Figure 1:
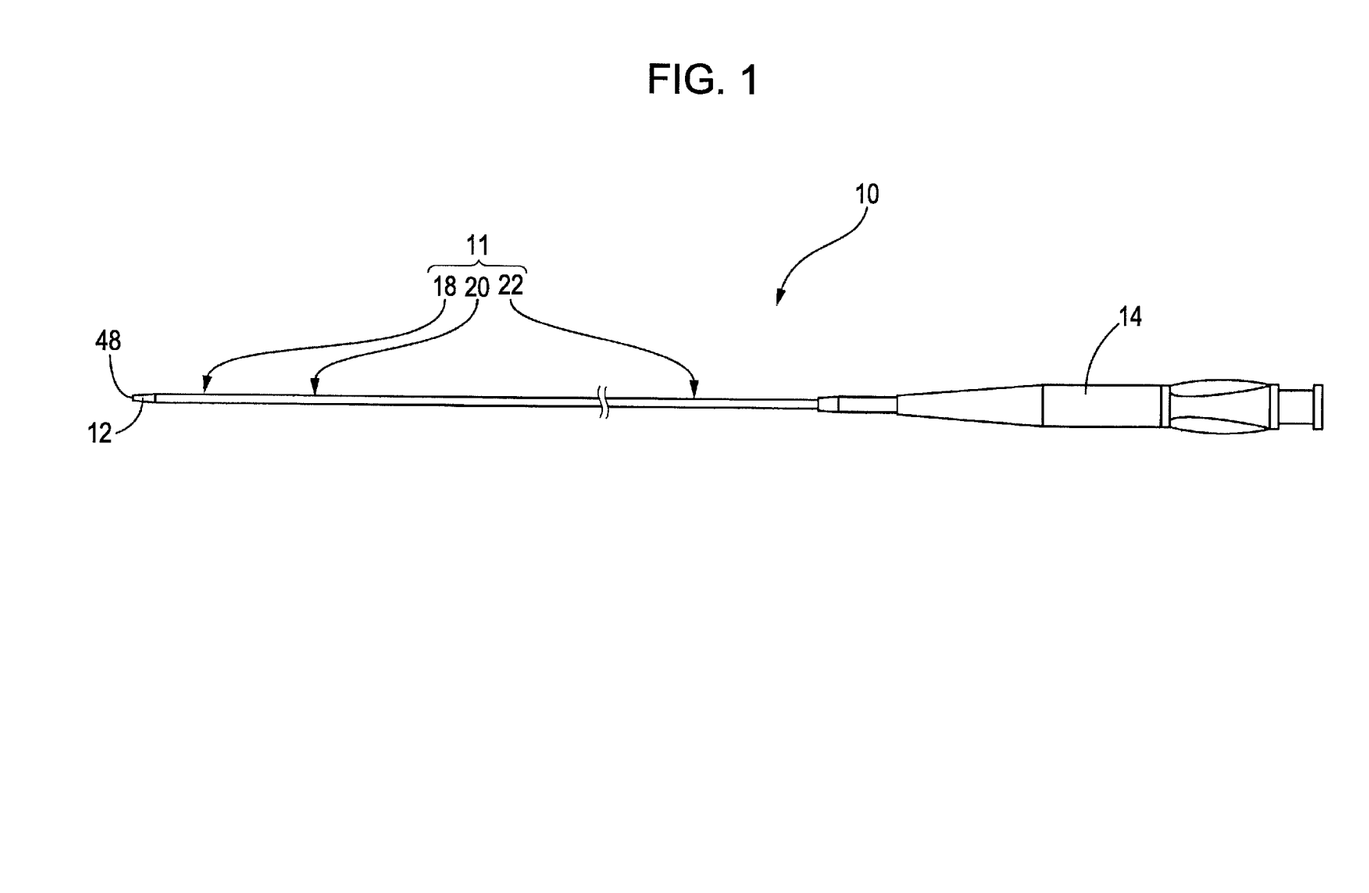
FIG. 1 is a plan view showing a catheter having a structure according to an embodiment of the invention.

FIG. 1 illustrates a catheter having a structure according to an embodiment of the invention. When the catheter is used, the catheter is inserted into a cardiac vessel having a stenosis and dilates the stenosis in the vessel. Referring to FIG. 1, a catheter 10 in this embodiment includes a catheter body 11, a soft tip 12 provided at the distal end (distal point) of the catheter body 11, and a connector 14. The proximal end of the catheter body 11 is attached to the connector 14.

Figure 2:
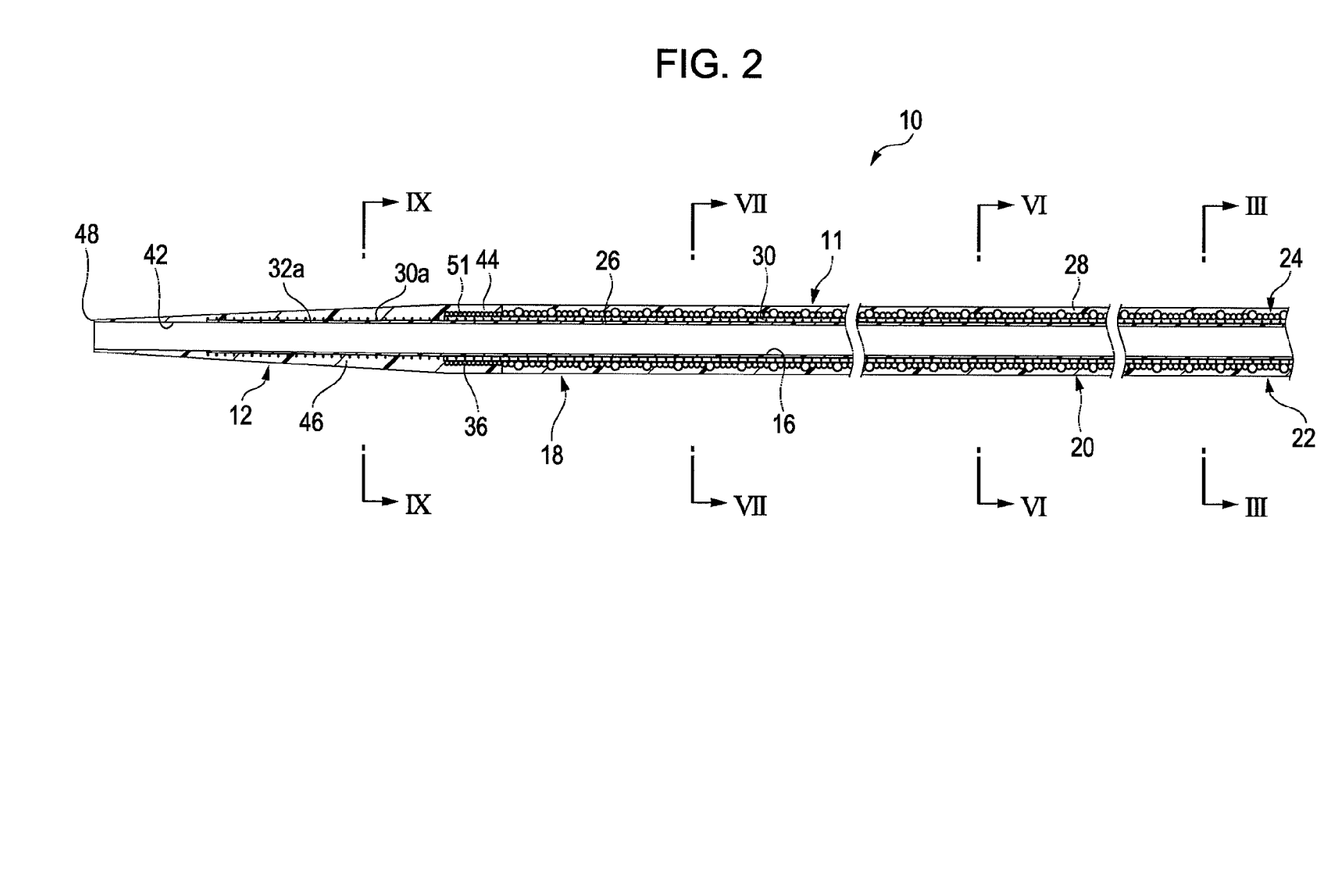
FIG. 2 is an enlarged view partly showing a longitudinal section of the catheter in FIG. 1.

In particular, referring to FIGS. 1 and 2, the catheter body 11 is a long hollow member having a lumen 16 into which a guidewire is inserted. The catheter body 11 has a full length of about 1500 mm. A part of the catheter body 11 extending from the distal end of the catheter body 11, at which the tip 12 is attached, by a distance of about 200 mm defines a distal section 18. The distal section 18 has an outer diameter of about 0.88 mm (0.85 to 0.90 mm). A part of the catheter body 11 extending from the proximal end of the distal section 18 by a distance of about 600 mm defines a middle section 20. The middle section 20 has a slightly larger outer diameter than the distal section 18. Further, a part of the catheter body 11 extending from the proximal end of the middle section 20 to the proximal end of the catheter body 11, which is attached to the connector 14, defines a proximal section 22. The proximal section 22 has a larger outer diameter than the middle section 20.

In the catheter body 11 of this embodiment, the distal section 18 has an outer diameter of about 0.88 mm, which corresponds to an outer diameter of a balloon catheter, which is typically used for an operation in cardiac catheter treatment. Since the distal section 18 has an outer diameter of about 0.88 mm, the catheter 10 can be used with various kinds of operations in cardiac catheter treatment. Also, the catheter with the distal section 18 having the outer diameter of about 0.88 mm may be modified as a standard catheter, so that the design of the catheter, such as the outer diameter, can be changed relatively easily. Thus, the catheter 10 of this embodiment may be advantageously used with various operations for organs other than the heart, which can be carried out even if a catheter 10 includes a distal section 18 having a larger outer diameter than 0.88 mm.

Figure 3:
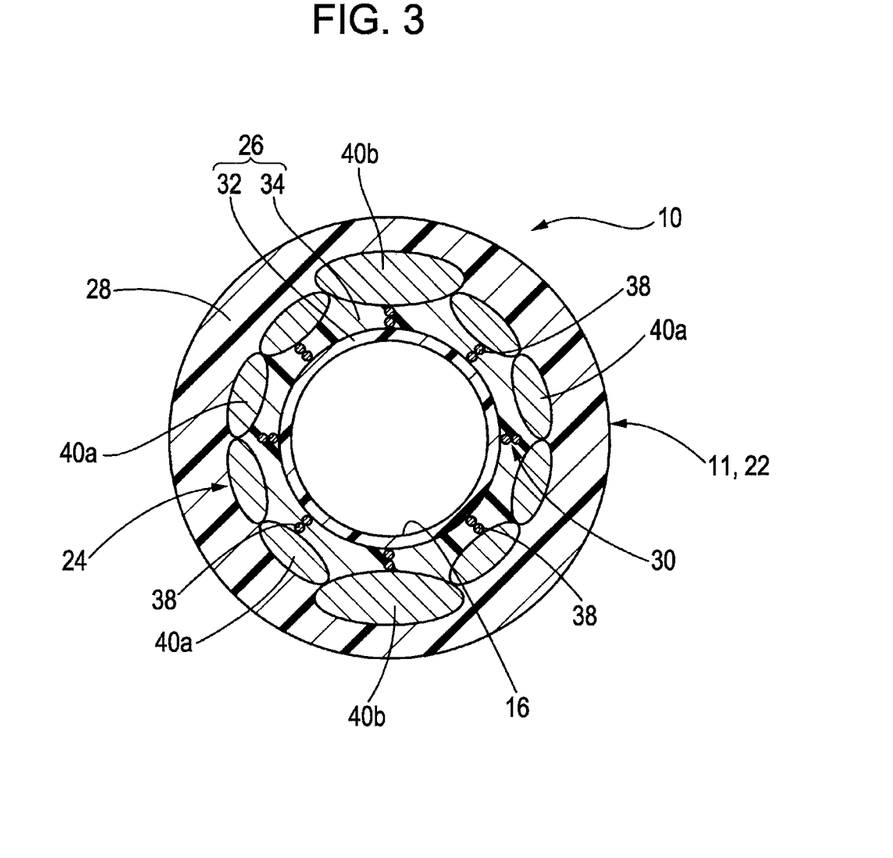
FIG. 3 is an enlarged cross sectional view showing an end face taken along line in FIG. 2.

Referring to FIGS. 2 and 3, the catheter body 11 includes a hollow coil 24, an inner resin layer 26 with which an inner peripheral surface of the coil 24 is coated, an outer resin layer 28 with which an outer peripheral surface of the coil 24 is coated, and a braid 30 embedded in the inner resin layer 26.

The inner resin layer 26 further includes an innermost layer 32 and a middle layer 34 arranged on the outer side of the innermost layer 32. The innermost layer 32 has a tube shape arranged at the innermost side of the catheter body 11 and extending over the full length of the catheter body 11. An inner bore of the innermost layer 32 defines a lumen 16 of the catheter body 11. The innermost layer 32 axially extends from the distal end of the catheter body 11. This extending portion defines a first inner-layer extending portion 32a (hereinafter, referred to as first extending portion 32a) located at the inner periphery of the tip 12. The first extending portion 32a is of sufficient length to reach a position near the distal end of the tip 12 (see FIG. 8). The resin material of the innermost layer 32 is not particularly limited, and may be appropriately selected from flexible and properly soft resin materials. For example, polytetrafluoroethylene (PTFE) with good lubricity is preferably used regarding sliding performance of a guidewire.

The middle layer 34 is arranged between the innermost layer 32 and the coil 24 and extends over the full length of the catheter body 11. The middle layer 34 axially extends from the distal end of the catheter body 11. The extending portion defines a second inner-layer extending portion 36 (hereinafter, referred to as second extending portion 36) located at the inner periphery of the tip 12 (see FIG. 8). The second extending portion 36 which is the extending portion of the middle layer 34 into the tip 12 has a smaller length than the first extending portion 32a which is the extending portion of the innermost layer 32 into the tip 12. The second extending portion 36 extends within a short length from the proximal end of the tip 12. Hence, the first extending portion 32a of the innermost layer 32 and the second extending portion 36 of the distal section of the middle layer 34 define an inner peripheral portion at the proximal section of the tip 12.

The resin material of the middle layer 34 is not particularly limited, and may be appropriately selected from flexible and properly soft resin materials, similarly to the innermost layer 32. For example, the material of the middle layer 34 may be polyamide elastomer.

Figure 4:
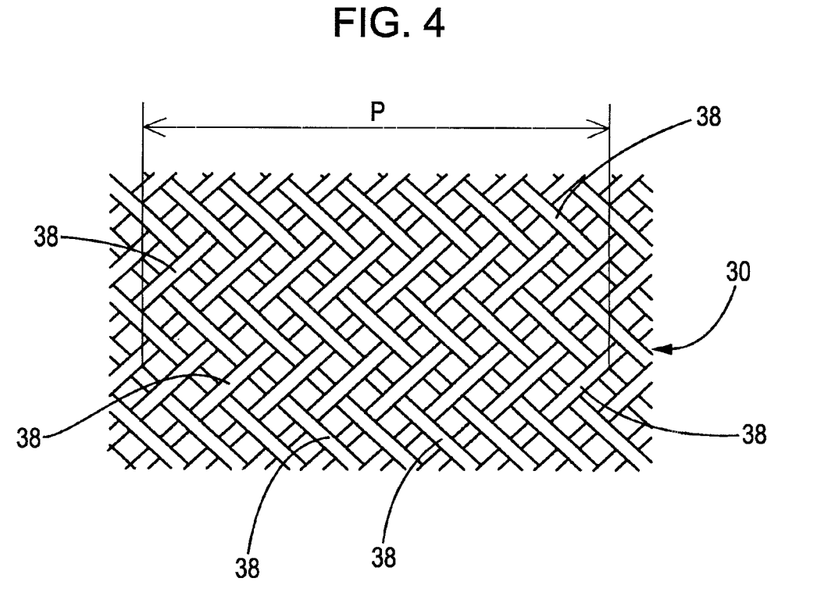
FIG. 4 is an enlarged view partly showing a braid of the catheter in FIG. 1.
Figure 5:
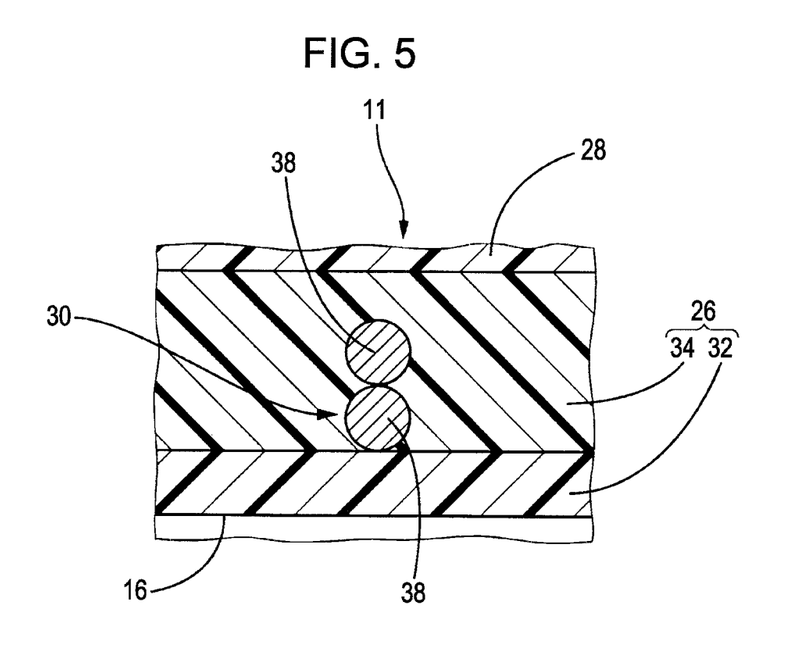
FIG. 5 is an enlarged view showing a part of FIG. 2, to explain an embedded condition of the braid in an inner resin layer.

Referring to FIG. 4, the braid 30 has a structure with a plurality of metal strands for braiding 38 (hereinafter, merely referred to as metal strands 38) alternately braided in a mesh-like manner. The braid 30 with the mesh-like structure surrounds the entire outer peripheral surface of the innermost layer 32 of the inner resin layer 26 in the catheter body 11 (see FIG. 3). Referring to FIG. 5, the braid 30 is embedded in the middle layer 34 of the inner resin layer 26.

Referring to FIG. 2, the braid 30 axially extends from the distal end of the catheter body 11, thereby defining an extending portion 30a, similarly to the innermost layer 32 of the inner resin layer 26. The extending portion 30a is embedded in the inner peripheral portion of the tip 12 while surrounding the full length of the outer peripheral surface of the first extending portion 32a of the innermost layer 32 extending from the distal end of the catheter body 11. Since the second extending portion 36 defines the inner peripheral portion at the proximal section of the tip 12, a part of the extending portion 30a of the braid 30 extending into the tip 12 and located at the proximal section of the tip 12 is embedded in the middle layer 34 of the second extending portion 36 (see FIG. 8).

In this embodiment, the braid 30 axially extends from the proximal section of the tip 12 over the full length of the catheter body 11 across the boundary between the tip 12 and the catheter body 11. The braid 30 is embedded in both the proximal section of the tip 12 and the catheter body 11. The braid 30 is positioned between the innermost layer 32 of the inner resin layer 26 and the coil 24 in the catheter body 11.

The metal material of the metal strands 38 for the braid 30 is not particularly limited, and, for example, strand members made of tungsten or stainless, may be preferably used as the metal strands 38. In particular, a strand member made of tungsten may be preferably used because of good visibility in radioscopy.

The braid 30 axially extends across the boundary between the catheter body 11 and the tip 12 as described above. Since the coil 24 is provided at the boundary, stresses may be likely concentrated at the boundary when an operation with the catheter 10 is carried out (which will be described later). Thus, the braid 30 needs to have a sufficiently high strength. Meanwhile, the braid 30 is provided in the catheter body 11 and in the soft tip 12. Thus, the braid 30 preferably has flexibility in addition to a high strength.

Owing to this, the metal strands 38 for the braid 30 preferably has a tensile strength (tensile rupture stress) of 1300 N/mm$^2$ measured under Annex B in ISO10555-1. If the metal strands 38 for the braid 30 have the tensile strength of 1300 N/mm$^2$, the strength at the boundary between the catheter body 11 and the tip 12 can be advantageously increased without the flexibility of the tip 12 being degraded. If the flexibility is more important than the strength for the braid 30, a braid 30 with metal strands 38 having a tensile strength of about 1400 N/mm$^2$ may be used. This embodiment uses a braid 30 formed of metal strands 38 having a tensile strength ranging from 3100 to 3600 N/mm$^2$ since the strength is more important than the flexibility.

The size of the metal strands 38 is not particularly limited, and may be appropriately determined on the basis of the sizes (outer diameters) etc. of the catheter body 11 and the tip 12. In this embodiment, the metal strands 38 each have a diameter of about 0.023 mm. The braid 30 is formed by alternately braiding the metal strands 38 such that 8×8, i.e., a total of 16 metal strands 38, are arranged in a unit part of the braid 30 corresponding to a pitch (dimension indicated by P in FIG. 4) of about 1 mm. The pitch corresponds to a length of a single metal strand 38 wound by one turn. In this embodiment, the braid 30 has a structure in which the plurality of metal strands 38 are braided. For example, the braid 30 may be formed by braiding various strands such as resin strands, other than the metal strands 38. The number of strands and the braiding form of the strands for the braid 30 may be appropriately changed. In addition, the braid 30 alternatively has a coiled structure or a spiral structure in which a single wire is wound.

Figure 6:
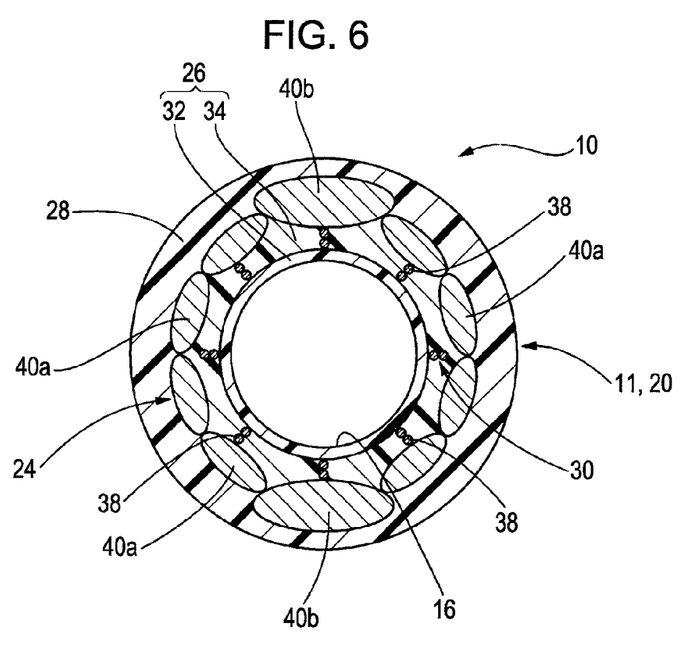
FIG. 6 is an enlarged cross sectional view showing an end face taken along line VI-VI in FIG. 2.
Figure 7:
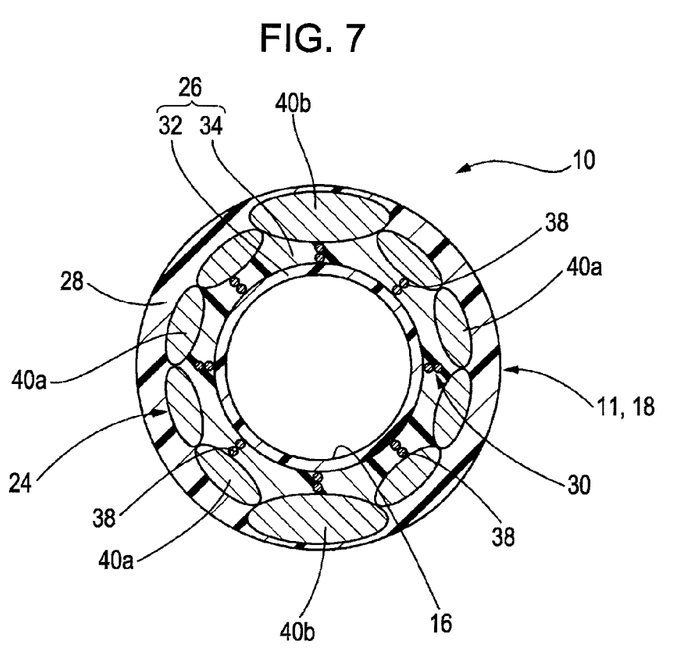
FIG. 7 is an enlarged cross sectional view showing an end face taken along line VII-VII in FIG. 2.

Referring to FIGS. 2 and 3, the coil 24 is a hollow coil with stranded wires formed by tightly stranding a plurality of (in this embodiment, ten) thin and long metal wires for coiling 40a, 40b (hereinafter, merely referred to as metal strands 40a, 40b) with a substantially circular cross section. After the plurality of metal strands 40a, 40b are stranded, the coil 24 is thermally processed by a known method, so that a residual stress as a result of stranding is removed. FIGS. 3, 6, and 7 illustrate the cross-sectional shapes of the metal strands 40a, 40b as ellipsoidal shapes because FIGS. 3, 6, and 7 illustrate cross sections orthogonal to the axial direction of the coil 24. The cross-sectional shapes of the metal strands 40a, 40b may be substantially circular shapes when the cross-sectional shapes are orthogonal to the axial direction of the metal strands 40a, 40b.

The metal material of the metal strands 40a, 40b of the coil 24 is not particularly limited. For example, the metal material of the metal strands 40a, 40b may be a superelastic alloy such as a Ni—Ti alloy, stainless steel, etc., or a combination of these materials.

Among the ten metal strands 40a, 40b made of such a metal material, eight metal strands 40a each have a diameter of about 0.07 mm, and the residual two metal strands 40b each have a diameter of about 0.12 mm, which is larger than the eight metal strands 40a. Hence, the coil 24 can have sufficiently high flexibility and high torque transmission performance, i.e., torque transmissivity. The diameter and number of the metal strands 40a, 40b of the coil 24 are not limited to those described above, and may be appropriately changed depending on the outer diameter etc. of the catheter body 11. For example, when a coil having an outer diameter of about 0.88 mm is formed like this embodiment, a plurality of metal strands for coiling having a uniform diameter of about 0.09 mm may be used.

To provide higher flexibility and torque transmission performance, the metal strands 40a, 40b of the coil 24 preferably have a tensile strength (tensile rupture stress) of 1300 N/mm² measured under Annex B in ISO10555-1. The tensile strength may more preferably range from about 1700 to 2100 N/mm². In this embodiment, the tensile strength is about 1900 N/mm².

The outer resin layer 28 is the outermost layer serving as the outer surface of the catheter body 11. The outer resin layer 28 surrounds the full length of the catheter body 11 while surrounding the entire outer peripheral surface of the coil 24 so that the metal strands 40a, 40b of the coil 24 are not exposed to the outside of the catheter body 11 through the outer surface.

Referring to FIGS. 3, 6, and 7, a part of the outer resin layer 28 corresponding to the outermost layer of the middle section 20 of the catheter body 11 has a larger thickness than a part of the outer resin layer 28 corresponding to the outermost layer of the distal section 18 of the catheter body 11 by a predetermined value, and a part of the outer resin layer 28 corresponding to the outermost layer of the proximal section 22 of the catheter body 11 has a larger thickness than the part of the outer resin layer 28 corresponding to the outermost layer of the middle section 20. The parts of the outer resin layer 28 corresponding to the distal section 18, the middle section 20, and the proximal section 22 of the catheter body 11 have hardnesses which increase in a step-like manner in that order. Hence, the proximal section 22, the middle section 20, and the distal section 18 of the catheter body 11 have flexibility which increases in a step-like manner in that order.

The resin material of the outer resin layer 28 is not particularly limited, and may be appropriately selected from flexible and properly soft resin materials similarly to the middle layer 34 of the inner resin layer 26. For example, the material of the outer resin layer 28 may be polyamide elastomer.

Figure 8:
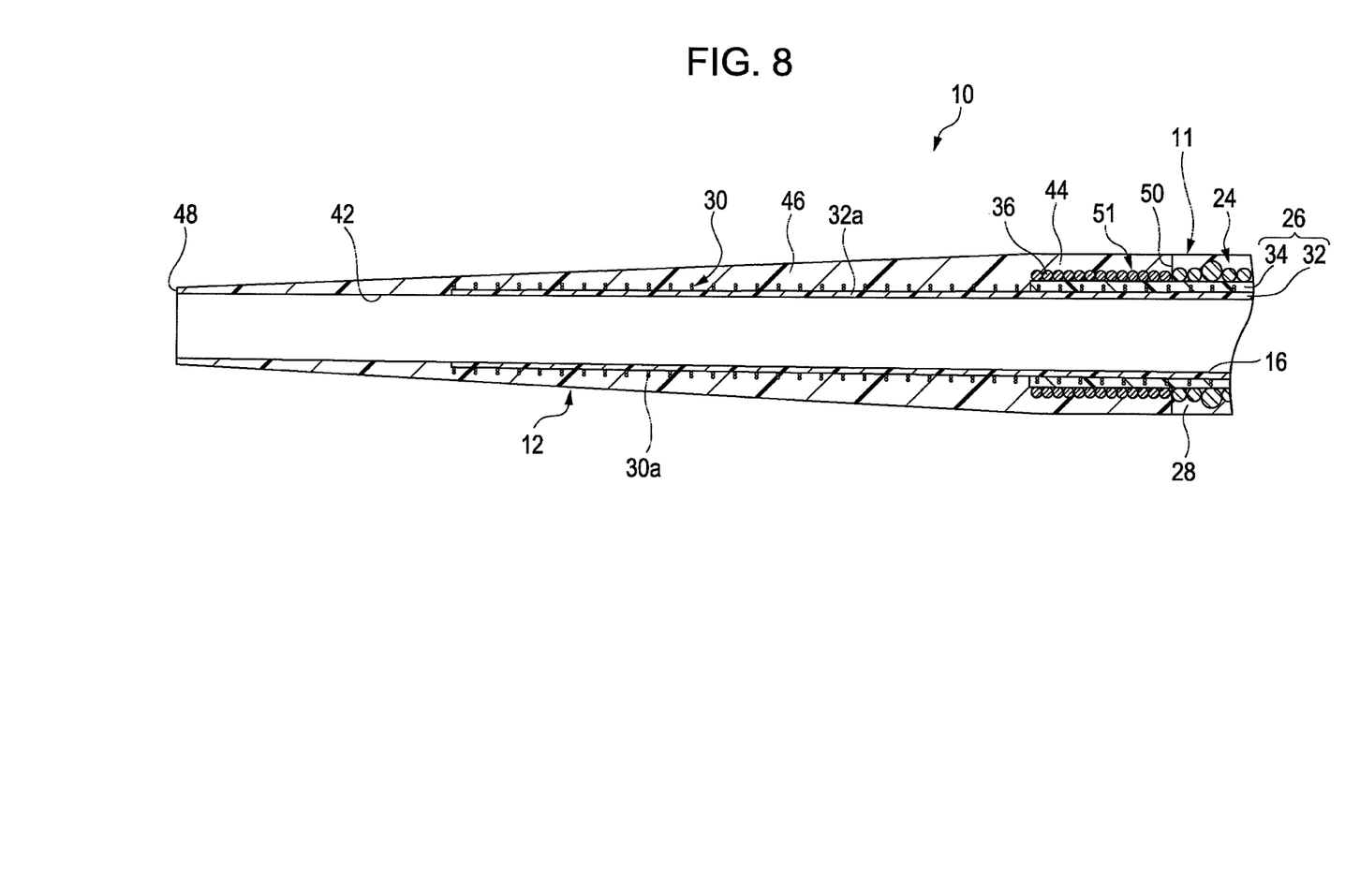
FIG. 8 is an enlarged view showing a part of FIG. 2, to explain an inner structure of a tip.
Figure 9:
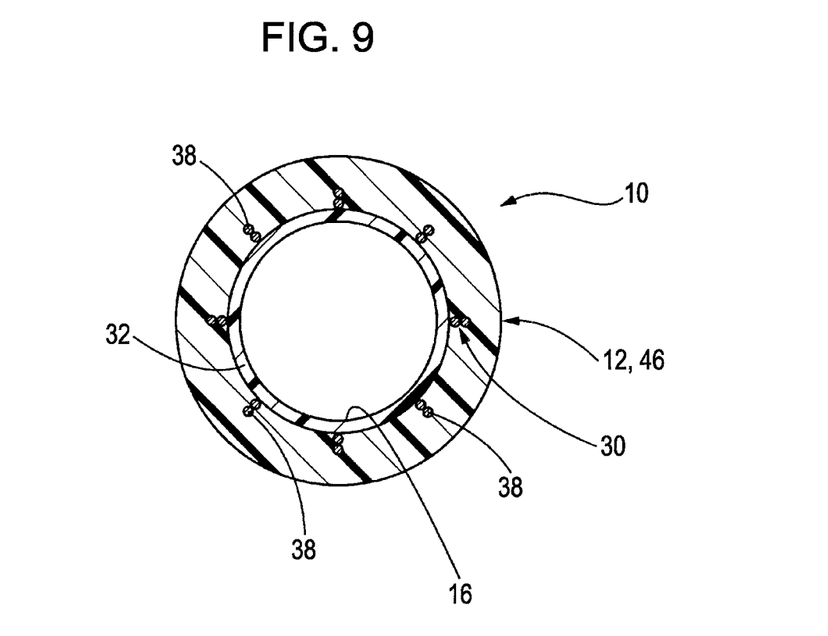
FIG. 9 is an enlarged cross sectional view showing an end face taken along line IX-IX in FIG. 2.

Referring to FIGS. 8 and 9, the tip 12 provided at the distal end of the catheter body 11 has a thin and long cylindrical shape having a lumen (inner bore) 42 communicating with the lumen 16 of the catheter body 11. The tip 12 is sufficiently softer than the catheter body 11. A proximal section of the tip 12 is a cylindrical section 44 having a cylindrical outer surface with a constant outer diameter. A distal section containing a middle section but excluding the cylindrical section 44 is a tapered section 46 having a tapered cylindrical outer peripheral surface with a diameter gradually decreasing toward the distal end (in a direction toward the leading end of the tip 12).

The resin material of the tip 12 is not particularly limited. Preferably, the resin material of the tip 12 may be softer than the resin materials of the inner resin layer 26 (the innermost layer 32 and the middle layer 34) and the outer resin layer 28. The resin material may be, for example, polyurethane elastomer with a Shore A hardness of about 80. In this embodiment, tungsten powder is mixed into the tip 12. This can advantageously increase the visibility of the tip 12 in radioscopy.

The lumen 42 of the tip 12 has a smaller inner diameter than the lumen 16 of the catheter body 11 by a predetermined value. The inner diameter of the lumen 42 of the tip 12 may be larger than the diameter (outer diameter) of a guidewire (not shown) by 5% to 20%, more preferably, by 5% to 10%. The guidewire is inserted through the lumen 42 of the tip 12 via the lumen 16 of the catheter body 11. That is, a gap occurs between the lumen 42 of the tip 12 and the outer peripheral surface of the guidewire when the guidewire is inserted through the lumen 42. The gap has a size ranging from 5% to 20%, more preferably, 5% to 10% of the diameter of the guidewire, in total length in the direction along the diameter of the guidewire. In this embodiment, assuming that a guidewire has a diameter of about 0.35 mm, the lumen 42 of the tip 12 has an inner diameter of about 0.38 mm.

In a state where the guidewire is inserted through the lumen 42 of the tip 12, the size of the step between the outer peripheral surface of a distal end 48 of the tip 12 and the outer peripheral surface of the guidewire extending from an opening at the distal end 48 is significantly decreased while the slidability of the guidewire in the lumen 42 is reliably maintained.

With the above structure, when an operation is carried out for insertion of the catheter 10 through a vessel with a small inner diameter, such as a collateral channel, which is soft and hence dilatable, advancing of the catheter 10 in the vessel over the guidewire can be easily and smoothly carried out, even though the inner diameter of the vessel is smaller than the outer diameter of the guidewire.

The cylindrical section 44 of the tip 12 has an outer diameter substantially equivalent to the outer diameter of the distal section 18 of the catheter body 11, and an axial length of about 0.8 mm. The cylindrical section 44 is integral with the distal section 18 of the catheter body 11. The second extending portion 36 (the innermost layer 32 and the middle layer 34) extending from the distal end of the catheter body 11 defines the inner peripheral portion of the cylindrical section 44 of the tip 12. A part of the braid 30 extending from the distal end of the catheter body 11 is embedded in the middle layer 34 of the second extending portion 36.

Thus, the cylindrical section 44 of the tip 12 is more flexible than the catheter body 11 including the coil 24. As described below, the cylindrical section 44 of the tip 12 is less flexible than the tapered section 46 of the tip 12 containing the distal section of the innermost layer 32 and the distal section of the braid 30 both located at the inner periphery of the tapered section 46 but not containing the middle layer 34. Thus, the tip 12 has flexibility which increases in a step-like manner toward the distal end 48 as compared with the flexibility of the catheter body 11. Therefore, a sudden change in flexibility of the catheter 10 at a boundary 50 between the distal end of the catheter body 11 and the proximal end of the tip 12 is eliminated. In addition, since the braid 30 extending from the distal end of the catheter body 11 is embedded in the cylindrical section 44 of the tip 12, the torque transmission performance at the boundary 50 between the distal end of the catheter body 11 and the proximal end of the tip 12 is advantageously increased. Further, the braid 30 can efficiently disperse a stress, which is likely concentrated at the boundary 50.

Also, a coil marker 51 is embedded in the cylindrical section 44 of the tip 12. The coil marker 51 surrounds the entire outer peripheral surface of the second extending portion 36. The coil marker 51 is formed of a coil in which a radiopaque single metal wire is wound. The coil marker 51 has an axial length substantially equivalent to the axial length of the second extending portion 36, and an outer diameter sufficiently smaller than the cylindrical section 44. Hence, the cylindrical section 44 functions as a marker for recognizing the position of the tip 12 in radioscopy. The coil marker 51 is formed of the coil, thereby advantageously preventing the flexibility of the cylindrical section 44 of the tip 12 from being excessively decreased because the coil marker 51 is embedded.

The tapered section 46 of the tip 12 has an outer peripheral surface with a diameter gradually decreasing toward the distal end 48 as described above. Also, the tapered section 46 has a thickness gradually decreasing toward the distal end 48. The first extending portion 32*a* of the innermost layer 32 extending from the distal end of the catheter body 11 defines the inner peripheral portion at the proximal section (part near the cylindrical section 44) of the tapered section 46. The extending portion 30*a* of the braid 30 extending from the distal end of the catheter body 11 is embedded in the tapered section 46. The part of the tapered section 46 at the distal end 48 does not contain the innermost layer 32 or the braid 30, and hence, that part has a very small thickness. Accordingly, the tapered section 46 of the tip 12 is softer and more flexible than the catheter body 11 and the cylindrical section 44 of the tip 12, and gradually becomes softer and more flexible toward the distal end 48.

The part of the tapered section 46 of the tip 12 near the distal end 48, the part which does not contain the distal section of the innermost layer 32 or the distal section of the braid 30 therein but is made of only the resin material of the tip 12, preferably has an axial length of 3.0 mm or smaller. The residual part of the tapered section 46 other than the part thereof near the distal end 48, that is the proximal section of the tapered section 46, the part which contains the extending portion 30*a* of the braid 30 therein, preferably has an axial length corresponding to 60% or more of the axial length of the entire tapered section 46, although the outer diameter of the catheter body 11 and the inner diameter of the tapered section 46 may limit the size of that part. Accordingly, the tip 12 can provide good torque transmission performance while maintaining good flexibility. In this embodiment, the part of the tapered section 46 at the distal end 48, the part which is made of only the resin material, has an axial length of 1.8 mm or smaller (or 2.0 mm or smaller being allowable). The extending portion 30*a* of the braid 30 extends in the tapered section 46 by an axial length corresponding to 64% or more of the axial length of the entire tapered section 46.

The tapered section 46 of the tip 12 has an outer diameter at the distal end 48 (minimum outer diameter) of about 0.44 mm. The lumen 42 has an inner diameter of 0.38 mm. That is, the tapered section 46 has a thickness at the distal end 48 of 0.03 mm. As described above, the step between the outer peripheral surface of the guidewire inserted through the lumen 42 of the tip 12 and the distal end 48 of the tip 12 is preferably significantly decreased. The thickness of the tapered section 46 at the distal end 48 determines the size of the step. Hence, in this embodiment, the tapered section 46 has the sufficiently small thickness of 0.03 mm at the distal end 48. The size of the step between the outer peripheral surface of the guidewire and the distal end 48 of the tip 12 is significantly decreased. The thickness of the tapered section 46 at the distal end 48 may be preferably a small thickness of 0.05 mm or smaller. However, regarding moldability of the tip 12, the thickness may range from 0.02 to 0.05 mm for practical use.

When the catheter 10 is advanced in a bent vessel over the guidewire, it is advantageous if the tapered section 46 defining the distal section of the tip 12 has a large axial length. However, if the axial length is excessively large, the distance from the distal end 48 of the tip 12 to the coil 24 of the catheter body 11 becomes excessively large, resulting in the torque transmission performance by the coil 24 to the distal end 48 of the tip 12 being decreased. In addition, decreasing the inclination of the tapered section 46 results in difficulty in pulling the distal end 48 of the tip 12 out of a stenosis when the distal end 48 is caught by the stenosis. Hence, the tapered section 46 of the tip 12 has an axial length which is three to ten times, more particularly, five to six times the outer diameter of the catheter body 11. Thus, in this embodiment, the tapered section 46 has an axial length of about 5.0 mm.

The catheter 10 of this embodiment with the above-mentioned structure is used for dilation of a cardiac vessel. Also, the catheter 10 may be used as a support catheter 10 to allow a guidewire to pass through the vessel. In any of the cases, when an operator advances the catheter 10 through a vessel, the operator may advance the catheter 10 while rotating the catheter 10.

Figure 10:
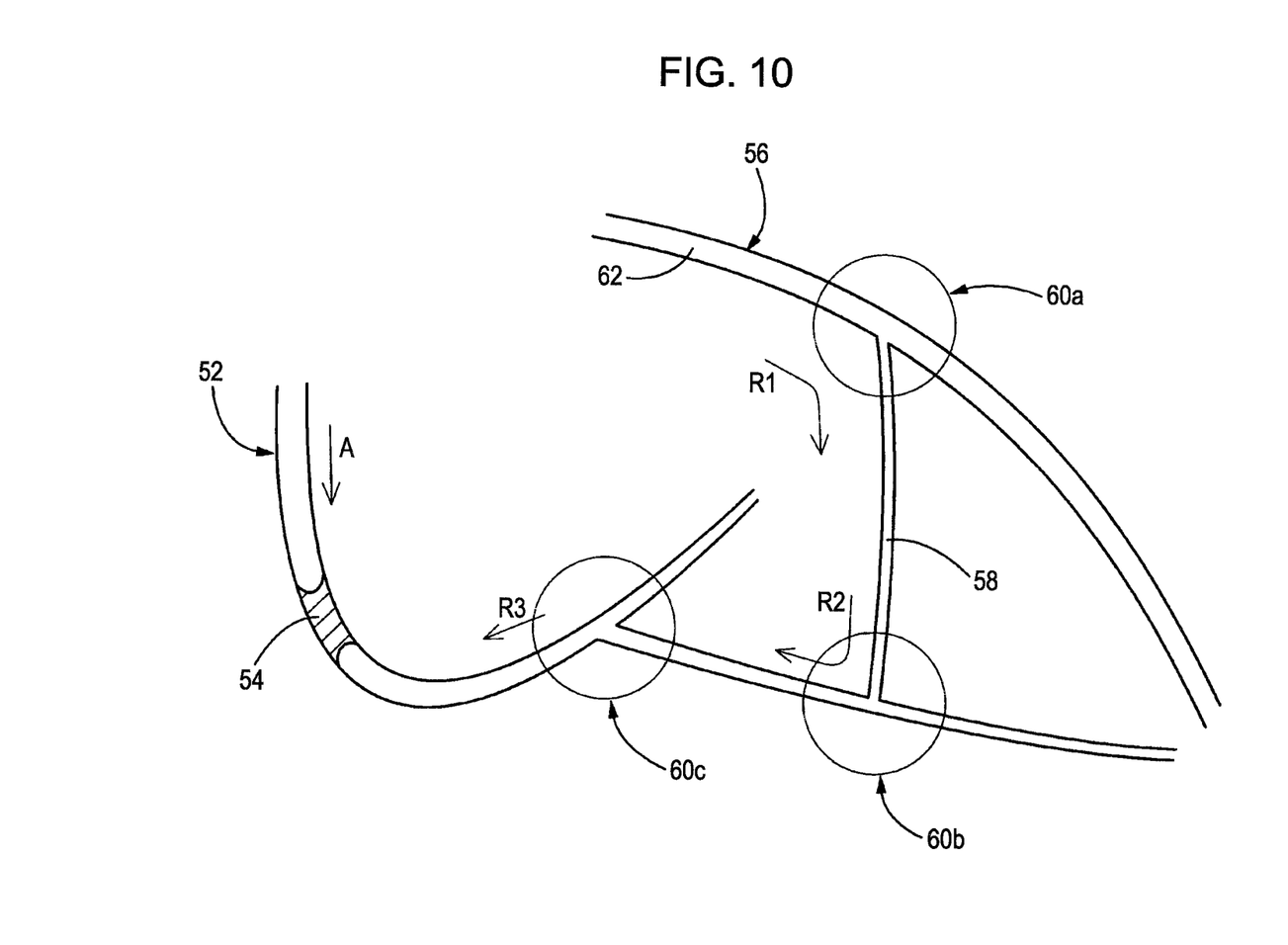
FIG. 10 is an explanatory view showing a stenosis in a vessel to be treated with the catheter in FIG. 1.

For example, referring to FIG. 10, when a stenosis 54 exists in a right coronary artery 52, a guidewire (not shown) is inserted in a direction indicated by arrow A, and a catheter (not shown) approaches the stenosis 54, for a treatment of the stenosis 54. This normal approach method to the stenosis 54 is called antegrade approach.

The catheter 10 of this embodiment is advantageous for retrograde approach, which is inverse to the antegrade approach. The retrograde approach is carried out such that the catheter 10 is advanced in directions indicated by arrows R1, R2, and R3 to the stenosis 54 through a collateral channel 58 extending from a left coronary artery 56 to the right coronary artery 52. The retrograde approach is very effective to a treatment for a lesion of a sever stenosis in a cardiac vessel, called chronic total occlusion (CTO).

When the retrograde approach is carried out, referring to FIG. 10, a catheter (not shown) has to pass through some (three in this embodiment) branches 60*a*, 60*b*, 60*c* to reach the stenosis 54. In particular, the branch 60*a* which branches from a main vessel 62 of the left coronary artery 56 and enters the collateral channel 58, and the branch 60*b* which branches from the collateral channel 58 and enters the right coronary artery 52 may each have an acute branching angle of 90° or smaller.

The operation procedure of an operation of the retrograde approach for making the catheter 10 approach the stenosis 54 will be described in detail below with reference to FIG. 10.

By the retrograde approach, a relatively soft guidewire is advanced to reach the stenosis 54. In the antegrade approach to make the guidewire approach the severe stenosis 54 such as the CTO and recannalize the stenosis 54, a stiff guidewire is frequently used. In contrast, in the retrograde approach to make the catheter 10 reach a position near the stenosis 54, it is advantageous to use a soft guidewire.

Once the soft guidewire has reached the stenosis 54, the catheter 10 is advanced within the left coronary artery 56 along the guidewire. Instead of the operation, another operation can be carried out as follows. While the soft guidewire slightly precedes the catheter 10, the distal point (the distal end 48 of the tip 12) of the catheter 10 is advanced to follow the guidewire up to a position slightly behind the distal point of the guidewire. While the catheter 10 supports the guidewire, the guidewire and the catheter 10 are alternately and gradually advanced.

Any of the operations advances the catheter 10 along the soft guidewire within the left coronary artery 56. Then, the catheter 10 is advanced toward the right coronary artery 52 from the main vessel 62 of the left coronary artery 56 through the collateral channel 58.

Since the catheter body 11 of the catheter 10 includes the coil 24 therein, when the operator rotates the proximal end of the catheter 10, the distal section of the catheter body 11 is reliably rotated. As described above, the torque transmission performance at the boundary 50 between the distal section of the catheter body 11 and the proximal section of the tip 12 is increased in the catheter 10. Hence, when the operator rotates the proximal end of the catheter 10 with the hand of the operator, the tip 12 of the catheter 10 is reliably rotated with the catheter body 11.

Hence, when the catheter 10 enters the collateral channel 58 and is advanced therethrough, the entire catheter 10 is reliably rotated, and the thin and soft collateral channel 58 can be gradually dilated. The catheter 10 can be smoothly advanced in the collateral channel 58.

The catheter 10 has the soft and elongated tip 12 at the distal end of the catheter 10. In addition, the size of the step between the outer peripheral surface at the distal end 48 of the tip 12 and the outer peripheral surface of the guidewire is significantly decreased. Although the two branches 60a, 60b with the acute branching angles are provided between the left coronary artery 56 and the right coronary artery 52 at both ends of the collateral channel 58, the tip 12 is elastically bent along the guidewire, and the catheter 10 smoothly enters the branches 60a, 60b, and passes through the branches 60a, 60b.

Further, when the tip 12 enters the two branches 60a, 60b with the acute branching angles, the tip 12 and the catheter body 11 is bent at acute angles, and also the catheter 10 is rotated. Although large bending stress and torsional stress act on and around the boundary 50 between the tip 12 and the catheter body 11, the stresses may be dispersed because the boundary 50 includes the braid 30. Moreover, the braid 30 increases the strength of the boundary 50 between the tip 12 and the catheter body 11.

In the catheter 10, the flexibility of the cylindrical section 44 of the tip 12 including the boundary 50 between the tip 12 and the catheter body 11 is slightly lower than the flexibility of the tapered section 46 at the distal end 48. A sudden change in flexibility is prevented between the tip 12 and the catheter body 11. This can advantageously decrease stresses generated because of bending and rotating at acute angles and concentrated at the boundary 50 between the tip 12 and the catheter body 11. Further, since the coil marker 51 is embedded in the cylindrical section 44 of the tip 12, the position of the catheter 10 in the vessel is clear in the radioscopy, and the sudden change in flexibility is further effectively decreased between the tip 12 and the catheter body 11.

When the soft guidewire has reached the stenosis 54 and then the catheter 10 has reached the stenosis 54, the soft guidewire is pulled out of the lumens 16, 42 of the catheter 10. Instead of the soft guidewire, a stiff guidewire is inserted through the lumens 16, 42. Then, with the inserted guidewire, a predetermined operation is continuously carried out.

When various operations are carried out after the catheter 10 reaches the stenosis 54, for example, if the catheter 10 is rotated while the distal end 48 of the tip 12 is caught by the stenosis 54, a large torsional stress acts on and around the boundary 50 between the tip 12 and the catheter body 11. The stress, however, is effectively dispersed because the boundary 50 includes the braid 30.

As described above, with the catheter 10 of this embodiment, the catheter operation using advanced techniques, for example, in a case where the catheter 10 is inserted through the vessel, like the collateral channel 58, having the branches 60a, 60b having the small inner diameters and the acute branching angles of 90° or smaller can be safely and smoothly carried out without the vessel or the catheter 10 being damaged.

The catheter body 11 of the catheter 10 includes the braid 30 continuously extending over the full length of the catheter body 11. For example, even when the coil 24 is formed of thin metal strands 40, the good torque transmission performance can be stably provided.

In order to assure that the catheter of this embodiment has the above-described advantageous features, some tests carried out by the inventors will be described in detail below.

Test 1

A catheter having the structure shown in FIGS. 1 and 2 was prepared. The dimensions and specifications of parts of the catheter were the same as those of the catheter of the embodiment.

Figure 11:
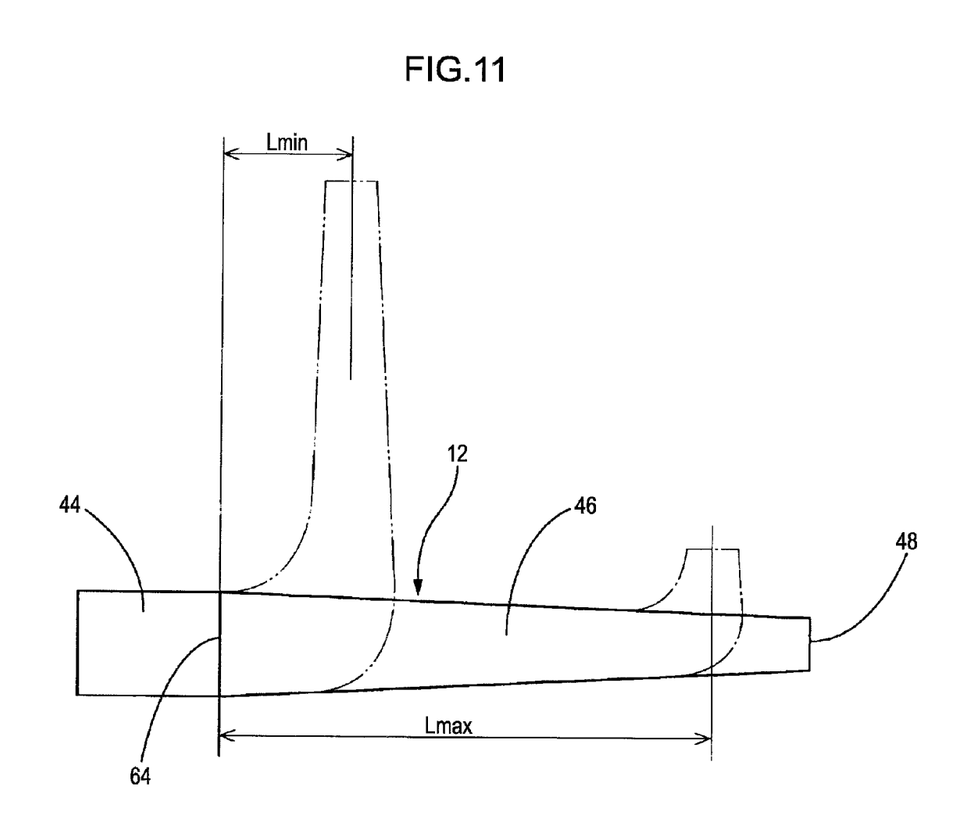
FIG. 11 is an explanatory view schematically showing a bent condition of the tip during a bending test carried out with the catheter in FIG. 1.

The catheter, in which the catheter body 11 was fixed not to be displaced, was used. Referring to FIG. 11, the tapered section 46 was gradually bent at a boundary 64 between the cylindrical section 44 (axial length: 0.8 mm) and the tapered section 46 (axial length: 5.0 mm) of the tip 12, from the distal end 48. Then, the axial length of the tip 12 from the boundary 64 to the bent part in which the distal end 48 of the tapered section 46 became orthogonal to the proximal section of the tapered section 46 was measured.

As a result, a maximum Lmax of the length was 4.0 mm whereas a minimum Lmin was 1.3 mm. Thus, it was found that the tip 12 can be bent orthogonally within a range of about 2.7 mm. To allow a catheter to smoothly pass through a branch at a branching angle of 90° or smaller of a vessel, generally, the maximum Lmax is important, which is the length from the boundary 64 between the cylindrical section 44 and the tapered section 46 to the bent part while the tapered section 46 is orthogonally bent. The maximum Lmax needs to be 3.8 mm or larger. Also, the minimum Lmin of the length is preferably 2.5 mm or smaller. Owing to this, a catheter of this embodiment with a maximum Lmax of 4.0 mm and a minimum Lmin of 1.3 mm can smoothly pass through the branch of the vessel having the branching angle of 90° or smaller.

Test 2

Four catheters having the structure shown in FIGS. 1 and 2 were prepared. The four catheters served as Examples 1 to 4. The dimensions and specifications of parts of the catheters were the same as those of the catheter of the embodiment.

For comparison, two catheters were similar to that having the structure shown in FIGS. 1 and 2 except that the catheters include no braid 30. The two catheters served as Comparative Examples 1 and 2. The catheters according to Comparative Examples 1 and 2 each had ten metal strands 40a, 40b for a coil 24, and eight metal strands 40a of the ten metal strands 40a, 40b each had a diameter of 0.08 mm, whereas the residual two metal strands 40b each had a larger diameter of 0.13 mm than the eight metal strands 40a. The dimensions and specifications of parts of the catheters were the same as those of the catheter of the embodiment. The reason the diameters of the metal strands 40a, 40b of the catheters according to any of Comparative Examples 1 and 2 is larger than the diameters of the metal strands 40a, 40b of the catheters according to any of Examples 1 to 4 is because the catheters according to Comparative Examples 1 and 2 each allowed to have a larger arrangement space for the coil 24 by eliminating the braid 30 from Comparative Examples 1 and 2. Hence, the diameters of the metal strands 40a, 40b of Comparative Examples 1 and 2 can be increased.

Figure 12:
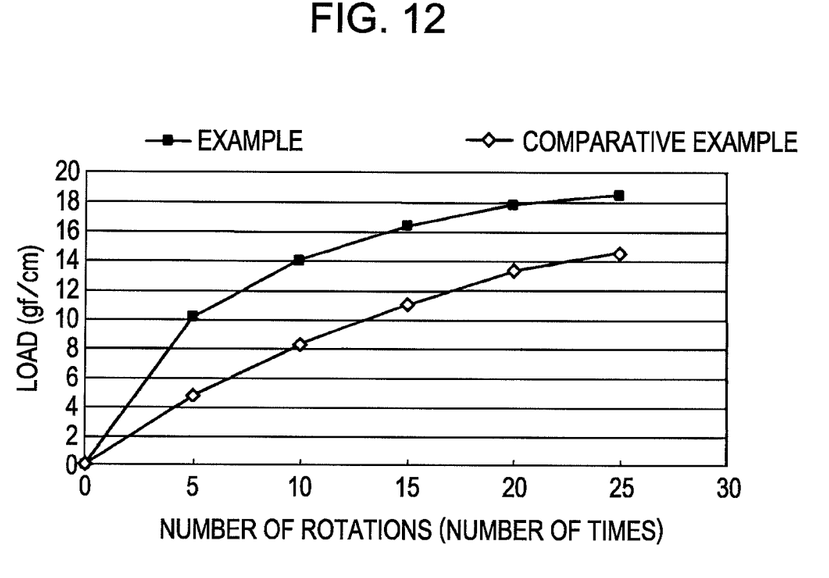
FIG. 12 is a graph showing the relationship between the number of rotations and a resulting torque load for each of the catheter in FIG. 1 and a catheter having the structure of the related art.

To measure torque transmission performances of the catheters according to Examples 1 to 4 and Comparative Examples 1 and 2, a torsion test was carried out for each of the catheters. The torsion test is carried out by rotating the distal section of each catheter through a torque gauge to apply a torsional force to the entire catheter while the proximal section of the catheter is fixed. The test was continued until any one of the ten metal strands of the coil of the catheter is broken. The relationship between the number of rotations of the catheter and the torque load measured by the torque gauge was checked for the catheter. Table 1 shows the test results of the catheters according to Examples 1 to 4. Table 2 shows the test results of the catheters according to Comparative Examples 1 and 2. Further, FIG. 12 is a graph showing the relationship between the average of the torque load per number of rotations and the number of rotations for each of the catheters according to Examples 1 to 4, and the relationship between the average of the torque load per number of rotations and the number of rotations for each of the catheters according to Comparative Examples 1 and 2. In FIG. 12, the graph for the examples shows the relationship between the average of the torque load per number of rotations and the number of rotations of the catheters according to Examples 1 to 4, and the graph for the comparative examples shows the relationship between the average of the torque load per number of rotations and the number of rotations of the catheters according to Comparative examples 1 and 2.

TABLE 1

| Number of rotations | Torque load (gf · cm) | | | | |
|---|---|---|---|---|---|
| (number of times) | Example 1 | Example 2 | Example 3 | Example 4 | Average |
| 0 | 0 | 0 | 0 | 0 | 0.0 |
| 5 | 11.5 | 9 | 10.5 | 10 | 10.3 |
| 10 | 15.5 | 13 | 14 | 13.5 | 14.0 |
| 15 | 17.5 | 15 | 17 | 16 | 16.4 |
| 20 | 19 | 17 | 18 | 17 | 17.8 |
| 25 | 19.5 | 17.5 | 19 | 18 | 18.5 |
| 30 | 22 | 18 | 20 | 19 | 19.8 |
| 35 | 23 | 20 | 21 | 20 | 21.0 |
| 40 | 23 | 21 | 23 | 21.5 | 22.1 |
| 45 | 25 | 23 | 23 | | 23.7 |
| 50 | | 23 | | | 23 |

TABLE 2

| Number of rotations | Torque load (gf · cm) | | |
|---|---|---|---|
| (number of times) | Comparative Example 1 | Comparative Example 2 | Average |
| 0 | 0.0 | 0.0 | 0.00 |
| 5 | 4.5 | 5.0 | 4.78 |
| 10 | 8.0 | 8.5 | 8.25 |
| 15 | 11.5 | 10.5 | 11.00 |
| 20 | 13.0 | 13.5 | 13.25 |
| 25 | | 14.5 | 14.50 |
| 30 | | | |
| 35 | | | |
| 40 | | | |
| 45 | | | |
| 50 | | | |

As shown in Tables 1 and 2, in each of the catheters according to Examples 1 to 4 with the structure of the embodiment, the metal strand of the coil is not broken until the catheter is rotated at least 40 times. In contrast, in each of the catheters according to Comparative Examples 1 and 2 without a braid, the metal strand of the coil is broken when the catheter is rotated 20 or 25 times. Consequently, it is clearly found that each of the catheters according to Examples 1 to 4 has good durability against torsional stress as compared with each of the catheters according to Comparative Examples 1 and 2.

Also, referring to FIG. 12, when the average of the torque load with a certain number of rotations of each of the catheters according to Examples 1 to 4 is compared with the average of the torque load with the same number of rotations of each of the catheters according to Comparative Examples 1 and 2, the catheter of any of Examples 1 to 4 has a higher torque load than the catheter of any of Comparative Examples 1 and 2 with any number of rotations. In particular, when the graph for the examples is compared with the graph for the comparative examples in FIG. 12, it is found that the inclination of the graph for the examples is larger than the inclination of the graph for the comparative examples with the rotations of 0 to 5 times. These results clearly show that the catheter with the braid according to any of Examples 1 to 4 having the structure of the embodiment has a higher torque transmission performance than that of the catheter without a braid according to any of Comparative Examples 1 and 2, particularly when the rotation is started.

The embodiment of the invention has been described above, however, the embodiment is merely an example of the invention, and the invention is not limited to the embodiment by the specific description relating to the embodiment.

For example, in the embodiment, the braid 30 axially extends from the proximal section of the tip 12 over the full length of the catheter body 11. However, the braid 30 does not have to extend over the full length of the catheter body 11. The braid 30 may extend from the proximal section of the tip 12 to at least the distal section of the catheter body 11. For example, in the catheter 10 of the embodiment, the braid 30 may extend from the boundary 50 between the tip 12 and the catheter body 11 toward the proximal side by about 20 mm.

In the embodiment, the metal strands 40b with the large diameter of the plurality of metal strands 40a, 40b of the coil 24 do not protrude from the outer peripheral surface of the catheter body 11 outward in the radial direction. However, the metal strands 40b with the large diameter may protrude outward in the radial direction from the outer peripheral surface of the catheter body 11 so that the metal strands 40b form a helical protrusion on the surface of the catheter body 11 by decreasing the thickness of the resin coating. With this structure, it is still preferable that the metal surfaces of the strands 40a, 40b do not protrude from the outer peripheral surface of the outer resin layer 28 not to be exposed to the outside.

In the embodiment, the thickness or hardness of the outer resin layer 28 is varied, and hence the flexibility of the distal section 18 of the catheter body 11 is higher than the flexibility of the proximal section 22 of the catheter body 11. Alternatively, the flexibility of the distal section 18 of the catheter body 11 can be increased by decreasing the rigidity of the distal section of the coil 24. A method of decreasing the rigidity of the distal section of the coil 24 may be electro-polishing or chemical polishing the distal section of the coil 24 to decrease the diameter of the metal strands 40a, 40b of the coil 24 and increase gaps among the metal strands 40a, 40b, or centerless grinding the distal section of the coil 24 to decrease the outer diameter of the coil 24 and decrease the thickness of the distal section of the coil 24.

Decreasing the rigidity of the distal section of the coil 24 can further reliably decrease a stress concentrated at the boundary between the proximal end of the tip 12 and the distal end of the coil 24 of the catheter body 11. A range of the distal section of the coil 24 subjected to electro-polishing or centerless grinding may be about 30 to 100 mm, more particularly, about 50 mm from the distal end toward the proximal section of the coil 24. The flexibility can be changed by adjusting the polishing amount by electro-polishing or the like.

The embodiment has provided a specific example in which the invention is applied to a catheter for treating a stenosis formed in a cardiac vessel. However, the invention can be advantageously applied to any of catheters for treating stenoses formed in vessels of organs other than the heart, or any of catheters inserted into the body for other purposes.

Although details are omitted, embodiments with various modifications, corrections, improvements added may be made by those skilled in the art. The present invention includes such embodiments without departing from the scope of the invention.

The present invention contains subject matter related to Japanese Patent Application No. 2008-264696 filed in the Japan Patent Office on Oct. 11, 2008, the entire contents of which are incorporated herein by reference.

What is claimed is:

1. A catheter comprising:
a catheter body including
   a hollow coil in which a plurality of metal strands are wound or stranded,
   an inner resin layer arranged on an inner surface of the hollow coil, the inner resin layer defining a lumen, and
   an outer resin layer arranged on an outer surface of the hollow coil;
a tip made of resin that is provided at a distal end of the catheter body, the tip having a tapered section with an outer diameter that continuously decreases from the distal end of the catheter body to a distal end of the tip, the tip having an inner bore communicating with the lumen of the inner resin layer, wherein the inner resin layer is made of at least two different layers and the tip is made of a material that is softer than a material of the at least two different layers; and
a braid extending in an axial direction of the catheter body across a boundary between a proximal end of the tip and the distal end of the catheter body, the braid also extending into the tapered section of the tip and being positioned between the inner resin layer and the hollow coil in the catheter body, wherein
   the hollow coil does not extend across the boundary.

2. The catheter according to claim 1, further comprising:
a second coil extending from the boundary toward the distal end of the tip, wherein a distance between a distal end of the second coil and the boundary is shorter than a distance between a distal end of the braid and the boundary.

3. The catheter according to claim 2, wherein the tapered section of the tip does not contain the second coil.

4. The catheter according to claim 1, wherein a distal end of the braid is distant from the distal end of the tip.

5. A catheter comprising:
a catheter body including
   a hollow coil in which a plurality of metal strands are wound or stranded,
   an inner resin layer arranged on an inner surface of the hollow coil, the inner resin layer defining a lumen, and
   an outer resin layer arranged on an outer surface of the hollow coil;
a tip made of resin that is provided at a distal end of the catheter body, the tip having: i) a tapered section with an outer diameter that decreases toward a distal end of the tip, and ii) an inner bore communicating with the lumen of the inner resin layer; and
a braid extending in an axial direction of the catheter body across a boundary between a proximal end of the tip and the distal end of the catheter body, wherein
   the hollow coil does not extend across the boundary,
   the inner resin layer includes an innermost layer and a middle layer that is positioned between the innermost layer and the hollow coil,
   a distal end of the innermost layer: i) extends across the boundary toward the distal end of the tip, and ii) is closer to the distal end of the tip than is a distal end of the middle layer,
   the braid is embedded within the middle layer in the catheter body, and
   a distal portion of the braid projects from the distal end of the middle layer toward the distal end of the tip, so that the distal portion of the braid is embedded within the tapered section tip.

6. The catheter according to claim 5, further comprising:
a second coil extending from the boundary toward the distal end of the tip, wherein a distance between a distal end of the second coil and the boundary is shorter than a distance between a distal end of the braid and the boundary.

7. The catheter according to claim 6, wherein a portion of the tip does not contain the second coil.

8. The catheter according to claim 5, wherein a distal end of the braid is distant from the distal end of the tip.

9. The catheter according to claim 5, wherein the tip is made of a material that is softer than a material of the innermost layer and a material of the middle layer.

* * * * *